(12) United States Patent
Yamago

(10) Patent No.: US 8,895,768 B2
(45) Date of Patent: Nov. 25, 2014

(54) CYCLOPARA (HETERO) ARYLENE COMPOUND AND METHOD FOR PRODUCING SAME

(75) Inventor: Shigeru Yamago, Uji (JP)

(73) Assignee: Kyoto University, Kyoto-shi (JP)

( * ) Notice: Subject to any disclaimer, the term of this patent is extended or adjusted under 35 U.S.C. 154(b) by 324 days.

(21) Appl. No.: 13/499,042

(22) PCT Filed: Sep. 29, 2010

(86) PCT No.: PCT/JP2010/066900
§ 371 (c)(1),
(2), (4) Date: May 17, 2012

(87) PCT Pub. No.: WO2011/040434
PCT Pub. Date: Apr. 7, 2011

(65) Prior Publication Data
US 2012/0220790 A1    Aug. 30, 2012

(30) Foreign Application Priority Data

Sep. 29, 2009   (JP) ................. 2009-224788

(51) Int. Cl.
| | | |
|---|---|---|
| C07F 19/00 | (2006.01) | |
| C07F 15/00 | (2006.01) | |
| C07C 15/20 | (2006.01) | |
| H01L 51/00 | (2006.01) | |
| C07C 1/32 | (2006.01) | |
| C07F 17/02 | (2006.01) | |
| C09K 11/06 | (2006.01) | |
| H05B 33/14 | (2006.01) | |
| C07C 13/64 | (2006.01) | |
| H01L 51/50 | (2006.01) | |

(52) U.S. Cl.
CPC .......... C07C 1/325 (2013.01); *C09K 2211/1007* (2013.01); H01L 51/005 (2013.01); C07F 15/0086 (2013.01); C07F 17/02 (2013.01); *H01L 51/5012* (2013.01); C07F 19/00 (2013.01); C09K 11/06 (2013.01); H05B 33/14 (2013.01); H01L 51/0058 (2013.01); *C07C 2103/90* (2013.01); *C07C 2103/18* (2013.01); *C07C 13/64* (2013.01)
USPC ................. 556/22; 556/136; 585/25; 585/27

(58) Field of Classification Search
CPC .......... C07F 17/00; C07F 19/00; C07C 15/20
USPC ................. 556/22, 136; 585/25, 27
See application file for complete search history.

(56) References Cited

PUBLICATIONS

Trans-Van et al., Organic Letters, vol. 16, No. 6, pp. 1594-1597 (2014).*

F. Zhang et al., "Giant Cyclo[n]thiophenes with Extended π Conjugation", Angewandte Chemie, International Edition, (2009), vol. 48, pp. 6632-6635, Cited in Office Action dated Nov. 20, 2013.
International Search Report of PCT/JP2010/066900, mailing date of Dec. 21, 2010.
Friederich, Rolf et al., "Auf dem Weg zu makrocyclischen para-Phenylenen", Chemische Berichte, 1993, vol. 126, p. 1723-1732.
Jagadeesh, Mavinahalli N. et al., "The Interplay of Angle Strain and Aromaticity: Molecular and Electronic Structures of [On] Paracyclophanes", Journal of Molecular Modeling, 2000, vol. 6, No. 2, p. 226-233.
Caskey, Douglas C. et al., "Toward Self-Assembled Surface-Mounted Prismatic Altitudinal Rotors. A Test Case: Molecular Rectangle", Organic Letters, 2004, vol. 6, No. 13, p. 2093-2096.
Yamago, Shigeru et al., "Synthesis of [8] Cycloparaphenylene from a Square-Shaped Tetranuclear Platinum Complex", Angewandte Chemie International Edition, 2010, vol. 49, No. 4, p. 757-759.
Jasti, Ramesh et al., "Synthesis, Characterization, and Theory of [9]-, [12]-, and [18] Cycloparaphenylene: Carbon Nanohoop Structures", Journal of the American Chemical Society, 2008, vol. 130, p. 17646-17647.
Takaba, Hiroko et al., "Selective synthesis of [12]Cycloparaphenylene", Angew. Chem. Int. Ed., 2009, vol. 48, p. 6112-6116.
Stang, P.J. et al., "Transition Metal Based Cationic Molecular Boxes. Self-Assembly of Macrocyclic Platinum( II ) and Palladium ( II ) Tetranuclear Complexes", J. AM. Chem. Soc., 1994, 116, pp. 4981-4982.
Fujita, M. et al., "Preparation of a Macrocyclic Polynuclear Complex, [(en) Pd (4,4'-bpy)]4(NO3)8, 1 Which Recognizes an Organic Molecule in Aqueous Media", J. Am. Chem. Soc. 1990, 112, pp. 5645-5647.

* cited by examiner

*Primary Examiner* — Porfirio Nazario Gonzales
(74) *Attorney, Agent, or Firm* — Westerman, Hattori, Daniels & Adrian, LLP

(57) ABSTRACT

Provided are a cyclopara(hetero)arylene compound and a method for producing the same. More specifically, provided is a cycloparaphenylene compound represented by Formula (I):

(I)

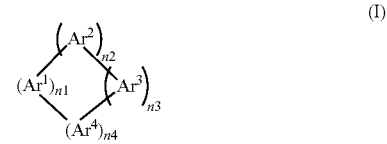

wherein $Ar^1$, $Ar^2$, $Ar^3$, and $Ar^4$ are the same or different, and represent an optionally substituted divalent aromatic group or an optionally substituted divalent heteroaromatic group, and
n1, n2, n3, and n4 are the same or different, and represent an integer of 1 or more.

6 Claims, No Drawings

CYCLOPARA (HETERO) ARYLENE COMPOUND AND METHOD FOR PRODUCING SAME

TECHNICAL FIELD

The present invention relates to a cyclopara(hetero)arylene compound and a method for producing the same.

BACKGROUND ART

Currently, there are two synthesis examples of cycloparaphenylenes. One is Bertozzi (USA, UC Berkeley) et al., who first succeeded in synthesizing cycloparaphenylenes (n=5, 8, 14) containing 9, 12, or 18 phenylenes in the following manner (NPL 1).

The feature of this method is to use sp3 carbons of cis-substituted cyclohexadiene-1,4-diol (compound 4) to form curves required for cycloparaphenylene, followed by conversion to sp2 carbons in the last step. This method has drawbacks in regard to low yield and low selectivity, including the time of producing ring products.

Itami (Nagoya University) et al. has reported the following method for selectively synthesizing cycloparaphenylene consisting of 12 benzene rings (NPL 2).

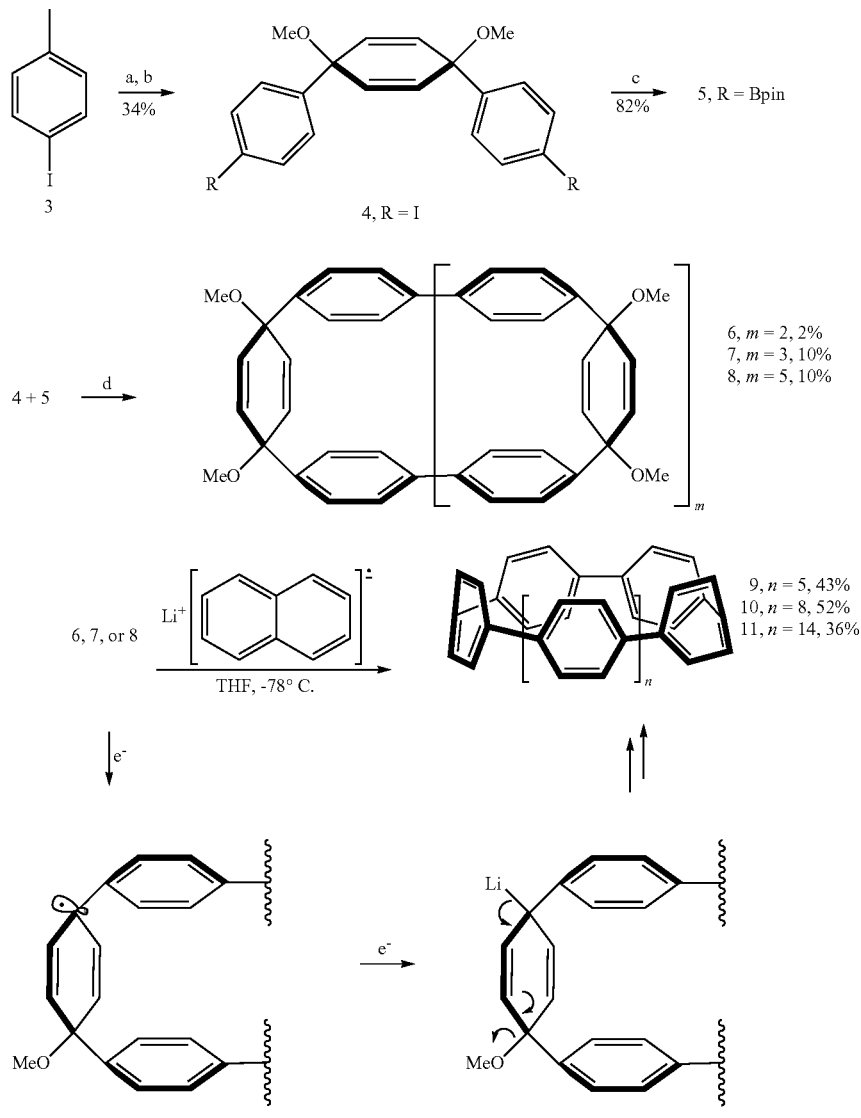

"a." Reagents and conditions: (a) (i) $n$BuLi, THF, -78° C., (ii) benzoquinone; (b) (i) NaH, THF, 0° C., (ii) MeI, 0° C. to rt; (c) (i) $n$Buli, THF, -78° C., (ii) isopropyl pinacol borate (Bpin), -78° C.; (d) Pd(PPh$_3$)$_4$, Cs$_2$CO$_3$, toluene/methanol (10:1), 80° C.

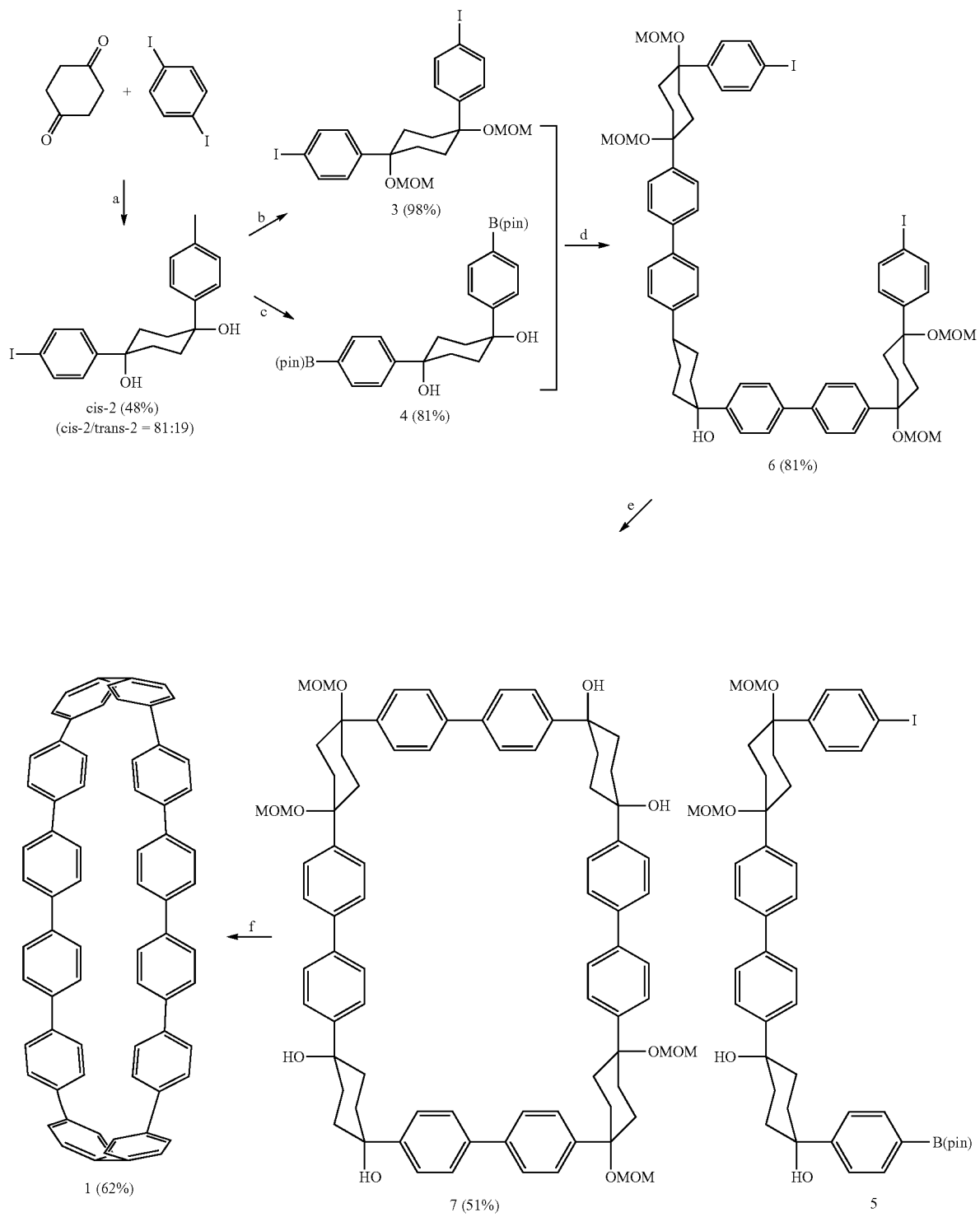

Scheme 3. Synthetic route toward 1.

Conditions and reagents: a) 1. 1,4-diiodobenzene (3.0 equiv), nBuli (3.0 equiv),THF, -78° C., 1 h; 2. cyclohexane-1,4-dione (1.0 equiv), RT, 2 hr; b) cis-2 (1.0 equiv), CH$_3$OCH$_2$Cl (7.6 equiv), iPr$_2$NEt (7.6 equiv), CH$_2$Cl$_2$, RT, 19 h; c) cis-2 (1.0 equiv), B$_2$(pin)$_2$ (2.4 equiv), [PdCl$_2$(dppf)] (3 mol %), KOAc (6.0 equiv), DMSO, 80 ° C., 13 h; d) 3 (10 equiv), 4 (1.0 equiv), [PdCl$_2$(dppf)] (10 mol %), NaOH (5.0 equiv), H$_2$O (16 equiv), 1,4-dioxane (8 mM with respect to 4), 60° C., 24 h; e) 6 (1.0 equiv), 4 (1.4 equiv), Pd (OAc)$_2$ (20 mol %), X-Phos (20 mol %), NaOH (5.0 equiv), H$_2$O (26 equiv), 1,4-dioxane (2 mM with respect to 6), 80° C., 24 h; f) 7 (1.0 equiv), pTsOH (1.O equiv), m-xylene, 150 ° C. (microwave), 30 min. DMSO = dimethyl sulfoxide, pin = pinacol, THF = tetrahydrofuran.

In this method, cis-cyclohexane-1,4-diol was used to form curves, and the compound was converted to sp2 carbon in the last step. Only cycloparaphenylene having 12 phenylenes can be selectively obtained; however, it is unclear whether compounds having other numbers of rings can be synthesized.

In both synthesis examples, the reaction conditions of the aromatization reaction in the last step are severe. More specifically, Bertozzi et al. used lithium naphthalenide (strongly basic), while Itami et al. added para-toluenesulfonic acid (highly acidic), followed by heating at 150° C.; accordingly, these methods are not suitable for the synthesis of cycloparaphenylene derivatives having various functional groups.

CITATION LIST

Non-Patent Literature

NPL 1: Jasti, R.; Bhattacharjee, J.; Neaton, J. B.; Bertozzi, C. R. J. Am. Chem. Soc. 2008, 130, 17646.

NPL 2: Takaba, H.; Omachi, H.; Yamamoto, Y.; Bouffard, J.; Itami, K. Angew. Chem. Int. Ed. 2009, 48, 6112.

SUMMARY OF INVENTION

Technical Problem

An object of the present invention is to provide a novel cyclopara(hetero)arylene compound and a method for producing the same.

Solution to Problem

A cyclopara(hetero)arylene compound is a molecule comprising a plurality of (hetero)aryls that are annularly bonded through two bonds having a 180° angle (typically, 1,4-(hetero)arylene bonds). The compound has a distorted conjugated structure, and is the minimum structural unit of armchair-type carbon nanotubes. Therefore, the synthesis and physical properties of the compound have attracted much attention. However, the synthesis of the compound is difficult, and there are thus only two synthesis examples so far (NPL 1 and NPL 2). The present inventor has developed a general method for synthesizing cyclopara(hetero)arylene compounds including an unreported number of rings, with a high yield and in a highly selective manner, using a completely different synthetic route from those of the conventional methods.

The present invention provides the following cyclopara(hetero)arylene compound, or a metal complex of the precursor thereof, and a method for producing the same.

Item 1. A compound represented by Formula (I):

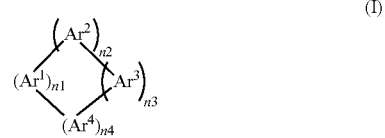

(I)

wherein $Ar^1$, $Ar^2$, $Ar^3$, and $Ar^4$ are the same or different, and represent an optionally substituted divalent aromatic group or an optionally substituted divalent heteroaromatic group, and n1, n2, n3, and n4 are the same or different, and represent an integer of 1 or more, with the proviso that in the case of $Ar^1$=$Ar^2$=$Ar^3$=$Ar^4$=1,4-phenylene, n1+n2+n3+n4 is a number other than 9, 12, and 18.

Item 2. The compound according to Item 1 represented by Formula (II):

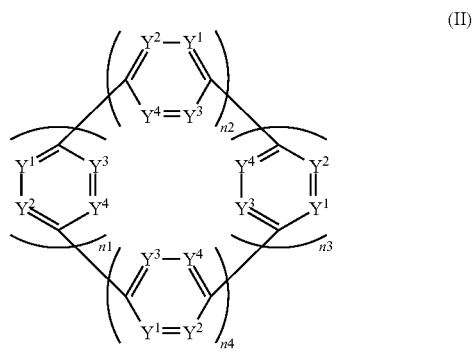

(II)

wherein $Y^1$ is the same or different, and represents CR' or N, $Y^2$ is the same or different, and represents $CR^2$ or N, $Y^3$ is the same or different, and represents $CR^3$ or N, $Y^4$ is the same or different, and represents $CR^4$ or N, $R^1$, $R^2$, $R^3$, and $R^4$ are the same or different, and represent hydrogen, alkyl, cycloalkyl, alkoxy, alkenyl, alkynyl, halogen, aryl, heterocyclyl, aralkyl, OH, CN, $NO_2$, COOH, $NH_2$, monoalkylamino, dialkylamino, acylamino, acyl, alkylcarbonyloxy, arylcarbonyloxy, alkoxycarbonyl, alkoxycarbonylamino, fluoroalkyl, perfluoroalkyl, carbamoyl, mono- or di-substituted carbamoyl, sulfamoyl, mono- or di-substituted sulfamoyl, or alkylsulfonylamino; adjacent $R^1$ and $R^2$, or $R^3$ and $R^4$, together with the carbon atoms to which they are attached, may form an optionally substituted 5- or 6-membered ring group, and n1, n2, n3, and n4 are the same or different, and represent an integer of 1 or more, with the proviso that in the case of $Y^1$=$Y^2$=$Y^3$=$Y^4$=CH, n1+n2+n3+n4 is a number other than 9, 12, and 18.

Item 3. The compound according to Item 1, wherein the divalent aromatic group is derived from an aromatic group selected from the group consisting of benzene, naphthalene, fluorene, indane, indene, azulene, anthracene, phenanthrene, phenalene, dihydroanthracene, indacene, dibenzosuberane, tetracene, and pyrene; and the divalent heteroaromatic group is derived from an heteroaromatic group selected from the group consisting of pyridine, pyrazine, pyrimidine, pyridazine, indole, quinoline, isoquinoline, tetrahydroquinoline, tetrahydroisoquinoline, benzothiazole, benzoxazole, benzoisoxazole, thianthrene, benzimidazole, chromene, xanthene, phenoxathiin, isoindole, indolizine, cinnoline, carbazole, β-carboline, phenanthridine, acridine, phenanthroline, phenothiazine, phenoxazine, phenanthridine, isochroman, chroman, phenazine, carbazole, indoline, and isoindoline.

Item 4. A compound represented by the following Formula (III):

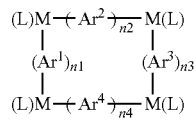
(III)

wherein $Ar^1$, $Ar^2$, $Ar^3$, and $Ar^4$ are the same or different, and represent an optionally substituted divalent aromatic group or an optionally substituted divalent heteroaromatic group, M is the same or different, and represents Pt, Pd, or Ni, L is the same or different, and represents a ligand capable of coordinating with M, and n1, n2, n3, and n4 are the same or different, and represent an integer of 1 or more.

Item 5. The compound according to Item 4 represented by the following Formula (IV):

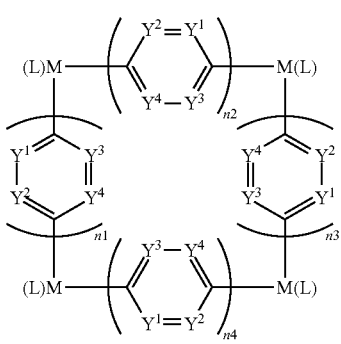
(IV)

wherein M is the same or different, and represents Pt, Pd, or Ni,

L is the same or different, and represents a ligand capable of coordinating with M, $Y^1$ is the same or different, and represents $CR^1$ or N, $Y^2$ is the same or different, and represents $CR^2$ or N, $Y^3$ is the same or different, and represents $CR^3$ or N, $Y^4$ is the same or different, and represents $CR^4$ or N, $R^1$, $R^2$, $R^3$, and $R^4$ are the same or different, and represent hydrogen, alkyl, cycloalkyl, alkoxy, alkenyl, alkynyl, halogen, aryl, heterocyclyl, aralkyl, OH, CN, $NO_2$, COOH, $NH_2$, monoalkylamino, dialkylamino, acylamino, acyl, alkylcarbonyloxy, arylcarbonyloxy, alkoxycarbonyl, alkoxycarbonylamino, fluoroalkyl, perfluoroalkyl, carbamoyl, mono- or di-substituted carbamoyl, sulfamoyl, mono- or di-substituted sulfamoyl, or alkylsulfonylamino; adjacent $R^1$ and $R^2$, or $R^3$ and $R^4$, together with the carbon atoms to which they are attached, may form an optionally substituted 5- or 6-membered ring group, and n1, n2, n3, and n4 are the same or different, and represent an integer of 1 or more.

Item 6. A method for producing a compound of Formula (I), comprising eliminating M(L) from a compound of Formula (III):

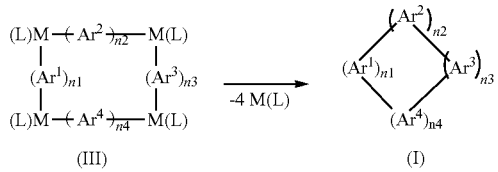

wherein $Ar^1$, $Ar^2$, $Ar^3$, and $Ar^4$ are the same or different, and represent an optionally substituted divalent aromatic group or an optionally substituted divalent heteroaromatic group, n1, n2, n3, and n4 are the same or different, and represent an integer of 1 or more, M is the same or different, and represents Pt, Pd, or Ni, and L is the same or different, and represents a ligand capable of coordinating with M.

Advantageous Effects of Invention

Cyclopara(hetero)arylene having various numbers of rings can be obtained selectively with a high yield. The reaction conditions are neutral, and the reaction proceeds under mild heating conditions; therefore, various functional groups can be introduced into (hetero)aromatic groups.

DESCRIPTION OF EMBODIMENTS

A cyclopara(hetero)arylene compound is a molecule comprising a plurality of optionally substituted divalent (hetero)aromatic groups that are annularly bonded through two bonds having a 180° angle (e.g., 1,4-bonds). The compound has a distorted conjugated structure, and is particularly the minimum structural unit of armchair-type carbon nanotubes; therefore, the synthesis and physical properties of the compound have attracted much attention. However, the synthesis of the compound is difficult, and there are thus only two synthesis examples so far (NPL 1 and NPL 2). The present inventors have developed a general method for synthesizing cycloparaphenylene including an unreported number of rings, with a high yield and in a highly selective manner, using a completely different synthetic route from those of the conventional methods.

In this specification, M represents Pt, Pd, or Ni, preferably Pt or Pd, and more preferably Pt. M may be a mixture of several metals, but is preferably a single metal. M is generally a divalent cation.

L represents a ligand capable of coordinating with M, and is a monodentate or bidentate olefin, amine, imine, pyridine, phosphine, arsine, or nitrile ligand. Examples thereof include cyclooctadiene (cod), norbornadiene (nbd), ethylene, ethylenediamine, and N-alkyl derivatives thereof, (2,2'-, 3,3'-, 4,4'-, 2,3'-, 2,4'-, or 3,4'-bipyridine, or alkyl-substituted derivatives thereof); 1,10-phenanthroline, triphenylphosphine, tributylphosphine, dimethylphenylphosphine, 1,1'-bis(diphenylphosphino)ethane, 1,1'-bis(diaryl)ferrocenylphosphine, such as 1,1'-bis(diphenylphosphino)ferrocene (dppf); diarylphosphinoethane, such as diphenylphosphinoethane; diphenylphosphinobutane, Xantphos, 2,2'-bis(diphenylphosphino)-1,1'-binaphthalene, tricyclohexylphosphine, cyclododecatriene, norbornene, 1,5-hexadiene, benzonitrile, butadiene, dimethyl acetylenedicarboxylate, dibenzylideneacetone, 1,5-bis(diphenylphosphino)pentane, diphenylmethylphosphine, and derivatives thereof. Preferable among these are cyclooctadiene, ferrocenylphosphine, and derivatives thereof. Examples of derivatives of the above ligands include, but are not limited to, derivatives in which the aryl group(s), such as phenyl, is(are) substituted with electron-attracting group(s), such as fluorine and trifluoromethyl. Examples of diphenylphosphinoethane derivatives include phosphinoethanes in which the phenyl group(s) is(are) tetra- or penta-substituted with electron-attracting groups (e.g., fluorine and trifluoromethyl), such as di(2,3,4,5,6-pentafluorophenyl)phosphinoethane, di(2,3,5,6-tetrafluorophenyl)phosphinoethane, and di(4-trifluoromethyl-2,3,5,6-tetrafluorophenyl)phosphinoethane.

Examples of X include halogen atoms, such as Cl, Br, and I.

Z is a group containing a metal capable of producing carbanion. Examples thereof include boron derivatives, such as $Sn(CH_3)_3$, $Sn(C_4H_9)_3$, Li, MgBr, MgCl, MgI, Cu, ZnBr, ZnI, $B(OCH_2CH_2O)$, and $B(OCMe_2CHe_2)$.

All of $Y^1$, $Y^2$, $Y^3$, and $Y^4$ may be carbon atom-containing groups ($CR^1$, $CR^2$, $CR^3$, and $CR^4$). The total number of N atoms of $Y^1$, $Y^2$, $Y^3$, and $Y^4$ is 0 to 4, preferably 0 to 3, and more preferably 0 to 2.

Examples of alkyl include linear or branched $C_{1-18}$ alkyl, such as methyl, ethyl, n-propyl, isopropyl, n-butyl, isobutyl, tert-butyl, n-pentyl, isopentyl, and hexyl.

Examples of cycloalkyl include $C_{3-10}$ cycloalkyl, such as cyclopropyl, cyclobutyl, cyclopentyl, cyclohexyl, and cycloheptyl. The ring may be partially substituted with a hetero element, or may have a substituent.

Examples of alkoxy include linear or branched $C_{1-18}$ alkoxy, such as methoxy, ethoxy, n-propoxy, isopropoxy, n-butoxy, isobutoxy, tert-butoxy, n-pentyloxy, isopentyloxy, hexyloxy, and polyethylene glycol derivatives.

Examples of alkenyl include linear, branched, or cyclic $C_{2-18}$ alkenyl, such as vinyl, 1-propenyl, 2-methyl-2-propenyl, isopropenyl, 1-, 2-, or 3-butenyl, 2-, 3-, or 4-pentenyl, 2-methyl-2-butenyl, 3-methyl-2-butenyl, 5-hexenyl, 1-cyclopentenyl, 1-cyclohexenyl, and 3-methyl-3-butenyl.

Alkynyl refers to a group having at least one triple bond. Examples thereof include linear, branched, or cyclic $C_{2-6}$ alkynyl, such as ethynyl, 1- or 2-propynyl, 1-, 2- or 3-butynyl, and 1-methyl-2-propynyl.

Examples of halogen atoms include F, Cl, Br, and I.

Aryl refers to a monocyclic or polycyclic group comprising a 5- or 6-membered aromatic hydrocarbon ring. Specific examples thereof include phenyl, naphthyl, toluyl, xylyl, fluorenyl, anthryl, biphenylyl, tetrahydronaphthyl, chromanyl, 2,3-dihydro-1,4-dioxanaphthalenyl, indanyl, and phenanthryl.

Examples of heterocyclyl include acridinyl, benzoimidazolyl, benzodioxolane, 1,3-benzodioxol-5-yl, benzofuranyl, benzothiophenyl, benzoxazolyl, benzothiazolyl, carbazolyl, cinnolinyl, 2,3-dihydrobenzofuranyl, dioxanyl, morpholino, furanyl, imidazolidinyl, imidazolinyl, imidazolyl, 1H-indazolyl, indolinyl, indolyl, 3H-indolyl, isoindolyl, isoquinolinyl, isothiazolyl, isoxazolyl, morpholinyl, 1,8-naphthyridinyl, oxadiazolyl, 1,3-oxathiolanyl, oxazolidinyl, oxazolyl, oxiranyl, parathiazinyl, phenazinyl, phenothiazinyl, phenoxazinyl, phthalazinyl, piperazinyl, piperidinyl, pteridinyl, pyranyl, pyrazinyl, pyrazolidinyl, pyrazolinyl, pyrazolo[1,5-c]triazinyl, pyrazolyl, pyridazinyl, pyridyl, pyrimidinyl, pyrimidyl, pyrrolyl, pyrrolidinyl, purinyl, quinazolinyl, quinolinyl, 4H-quinolizinyl, quinoxalinyl, tetrazolidinyl, tetrazolyl, thiadiazolyl, thiazolidinyl, triazolyl, thienyl, thiomorpholinyl, triazinyl, and triazolyl.

Examples of aralkyl include benzyl, phenethyl, naphthylmethyl, etc.

Examples of monoalkylamino include methylamino, ethylamino, n-propylamino, isopropylamino, n-butylamino, isobutylamino, tert-butylamino, n-pentylamino, isopentylamino, and hexylamino.

Examples of dialkylamino include dimethylamino, diethylamino, di-n-propylamino, diisopropylamino, di-n-butylamino, diisobutylamino, di-tert-butylamino, di-n-pentylamino, diisopentylamino, and dihexylamino.

Examples of acylamino include acetylamino, propionylamino, butyrylamino, isobutyrylamino, valerylamino, benzoylamino, etc.

Examples of acyl include acetyl, propionyl, butyryl, isobutyryl, valeryl, and benzoyl.

Specific examples of alkylcarbonyloxy include methylcarbonyloxy, ethylcarbonyloxy, n-propylcarbonyloxy, isopropylcarbonyloxy, n-butylcarbonyloxy, isobutylcarbonyloxy, tert-butylcarbonyloxy, n-pentylcarbonyloxy, isopentylcarbonyloxy, and hexylcarbonyloxy.

Specific examples of arylcarbonyloxy include phenylcarbonyloxy, naphthylcarbonyloxy, fluorenylcarbonyloxy, anthrylcarbonyloxy, biphenylylcarbonyloxy, tetrahydronaphthylcarbonyloxy, chromanylcarbonyloxy, 2,3-dihydro-1,4-dioxanaphthalenylcarbonyloxy, indanylcarbonyloxy, and phenanthrylcarbonyloxy.

Examples of alkoxycarbonyl include $C_{1-6}$ alkoxycarbonyl, such as methoxycarbonyl, ethoxycarbonyl, propoxycarbonyl, isopropoxycarbonyl, butoxycarbonyl, isobutoxycarbonyl, tertbutoxycarbonyl, pentyloxycarbonyl, isopentyloxycarbonyl, and hexyloxycarbonyl.

Examples of alkoxycarbonylamino include $C_{1-6}$ alkoxycarbonylamino, such as methoxycarbonylamino, ethoxycarbonylamino, propoxycarbonylamino, isopropoxycarbonylamino, butoxycarbonylamino, isobutoxycarbonylamino, tert-butoxycarbonylamino, pentyloxycarbonylamino, isopentyloxycarbonylamino, and hexyloxycarbonylamino.

Examples of fluoroalkyl include monofluoromethyl and difluoromethyl.

Examples of perfluoroalkyl include linear or branched perfluoroalkyl represented by $C_nF_{2n+1}$ (n is an integer of 1 to 6), particularly trifluoromethyl.

Examples of monoalkylcarbamoyl include methylcarbamoyl, ethylcarbamoyl, n-propylcarbamoyl, isopropylcarbamoyl, n-butylcarbamoyl, isobutylcarbamoyl, tert-butylcarbamoyl, n-pentylcarbamoyl, isopentylcarbamoyl, and hexylcarbamoyl.

Examples of dialkylcarbamoyl include dimethylcarbamoyl, diethylcarbamoyl, di-n-propylcarbamoyl, diisopropylcarbamoyl, di-n-butylcarbamoyl, diisobutylcarbamoyl, di-tert-butylcarbamoyl, di-n-pentylcarbamoyl, diisopentylcarbamoyl, and dihexylcarbamoyl.

Examples of monoalkyl-substituted sulfamoyl include methylsulfamoyl, ethylsulfamoyl, n-propylsulfamoyl, isopropylsulfamoyl, n-butylsulfamoyl, isobutylsulfamoyl, tert-butylsulfamoyl, n-pentylsulfamoyl, isopentylsulfamoyl, and hexylsulfamoyl.

Examples of dialkyl-substituted sulfamoyl include dimethylsulfamoyl, diethylsulfamoyl, di-n-propylsulfamoyl, diisopropylsulfamoyl, di-n-butylsulfamoyl, diisobutylsulfamoyl, di-tert-butylsulfamoyl, di-n-pentylsulfamoyl, diisopentylsulfamoyl, and dihexylsulfamoyl.

Examples of alkylsulfonylamino include methylsulfonylamino, ethylsulfonylamino, n-propylsulfonylamino, isopropylsulfonylamino, n-butylsulphonylamino, isobutylsulfonylamino, tert-butylsulphonylamino, n-pentylsulfonylamino, isopentylsulfonylamino, and hexylsulfonylamino.

Adjacent $R^1$ and $R^2$, or $R^3$ and $R^4$, together with the carbon atoms to which they are bonded, may form an optionally substituted 5- or 6-membered ring group. The term "adjacent" indicates a situation where the 5- or 6-membered ring group may be formed between adjacent groups bonded to the same aromatic or heteroaromatic ring (Case A below), or between one group and the closest group bonded to the adjacent aromatic or heteroaromatic ring (Case B below). The 5- or 6-membered ring group is saturated or unsaturated, and may be a hydrocarbon ring group or a ring group having at least one heteroatom (O, N, or S). The following examples show cases where adjacent $Y^1$ and $Y^2$ form a 5- or 6-membered ring group; however, $Y^3$ and $Y^4$ may also form a 5- or 6-membered ring group. Furthermore, the 5- or 6-membered ring group may be substituted with 1 to 3 substituents selected from alkyl, cycloalkyl, alkoxy, alkenyl, alkynyl, halogen, aryl, heterocyclyl, aralkyl, OH, CN, $NO_2$, COOH, $NH_2$, monoalkylamino, dialkylamino, acylamino, acyl, alkylcarbonyloxy, arylcarbonyloxy, alkoxycarbonyl, alkoxycarbonylamino, fluoroalkyl, perfluoroalkyl, carbamoyl, mono- or di-substituted carbamoyl, sulfamoyl, mono- or di-substituted sulfamoyl, and alkyl sulfonylamino.

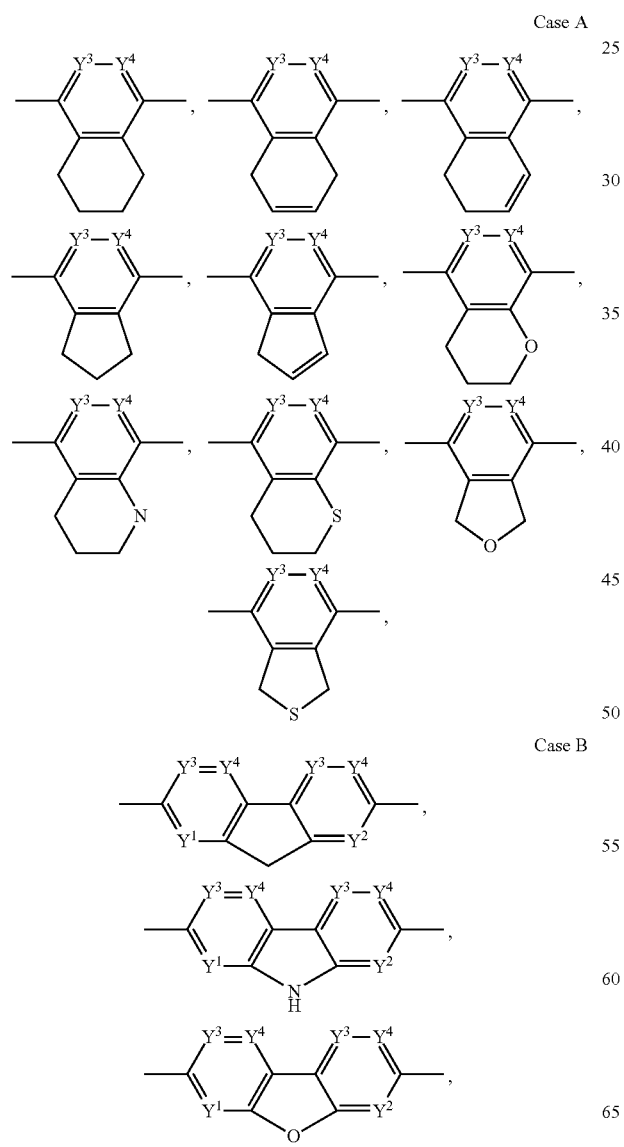

Divalent aromatic groups refer to monocyclic or polycyclic divalent groups containing a 6-membered aromatic hydrocarbon ring. Specific examples of aromatic groups include those having one or more rings, such as benzene, naphthalene, fluorene, fluorenone, fluorenol, indane, indene, azulene, anthracene, phenanthrene, phenalene, dihydroanthracene, indacene, dibenzosuberane, tetracene, and pyrene, which can bond to an adjacent (hetero)aromatic group at a position where the two bonds form a 180° angle, such as the 1- and 4-positions of the benzene ring, the 1- and 4-positions, 1- and 5-positions, or 2- and 6-positions of the naphthalene ring, the 1- and 4-positions, 1- and 5-positions, 1-and 6-positions, or 2- and 7-positions of the anthracene ring, the 1- and 4-positions, 1- and 6-positions, 2- and 7-positions, or 3- and 9-positions of the phenanthrene ring, the 1- and 4-positions of the fluorene ring, etc. When the divalent (hetero)aromatic group is composed of a plurality of unfused (hetero)aromatic groups, two or more (hetero)aromatic groups may be linked through a direct bond (e.g., biphenyl or bipyridyl), or by any divalent group, such as —CH═CH—, —C≡C—, —N═N—, or

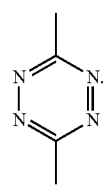

Divalent aromatic groups are obtained from the above aromatic groups by removing two hydrogen atoms bonded to each aromatic ring. In such a case, the two bonds of such a divalent aromatic group also form an angle of 180 degrees with each other. For example, in the case of -Ph-CH═CH-Ph- or -Ph-N═N-Ph-, there are the following aromatic groups:

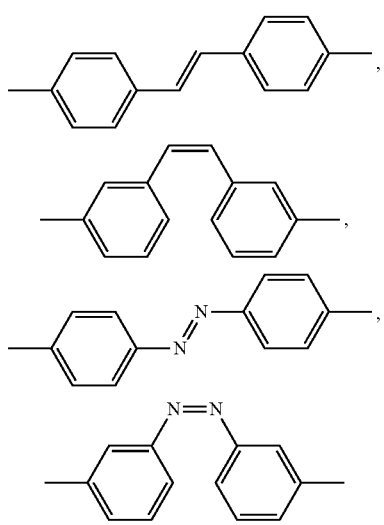

The above examples show two (hetero)aromatic groups linked through CH=CH— or —N=N—; however, the present invention also includes three or more (hetero)aromatic groups linked by a plurality of divalent groups. Moreover, the compound of the present invention, in which the (hetero)aromatic group is an diazobenzene derivative, is a preferred embodiment of the present invention.

The following shows examples of the positions of the two bonds of the divalent aromatic group of the present invention.

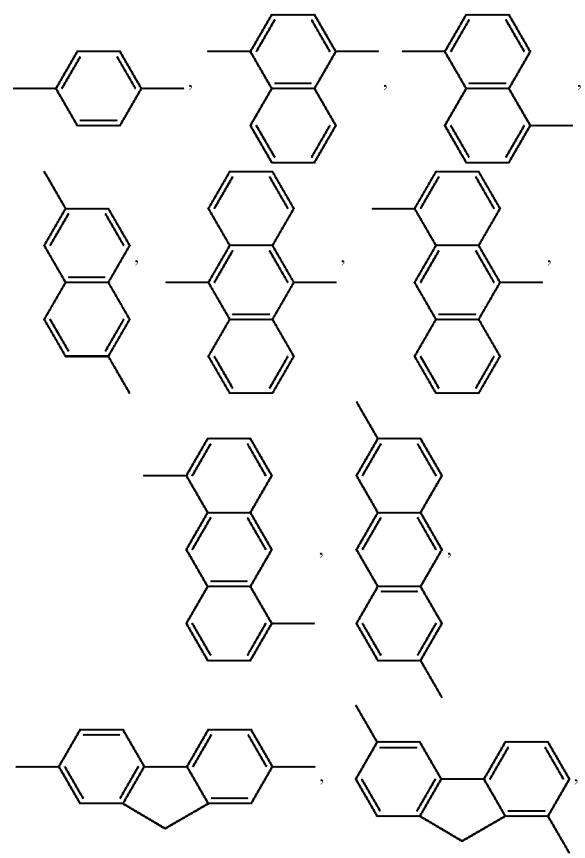

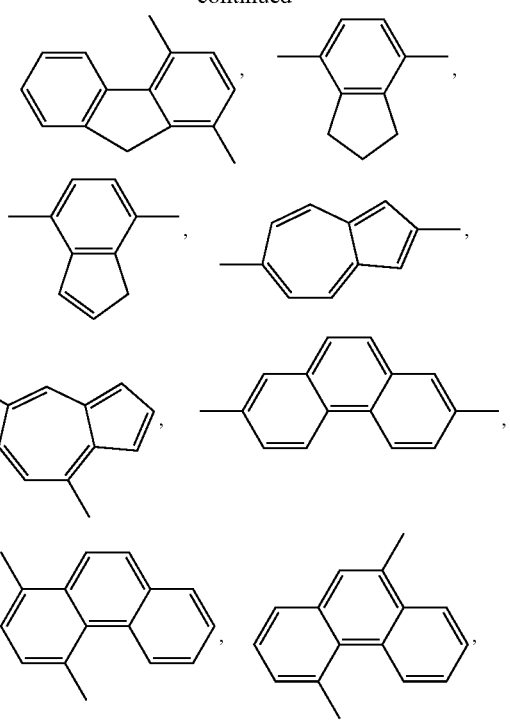

-continued

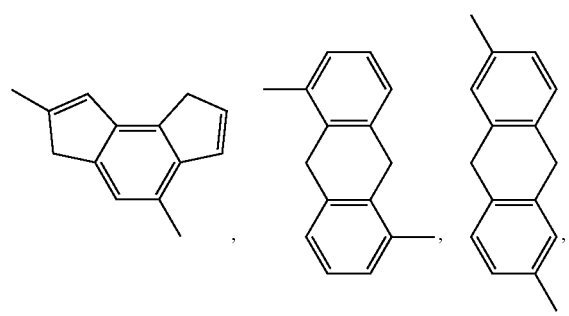

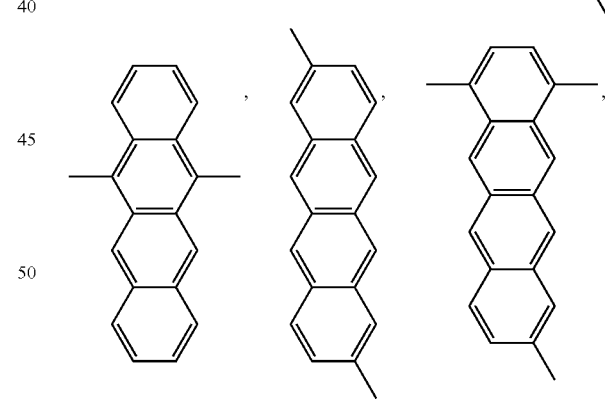

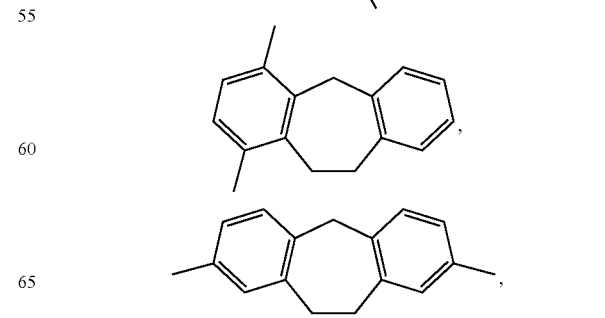

-continued

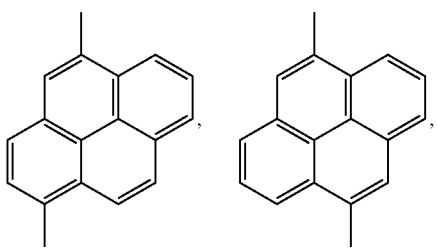

Divalent heteroaromatic groups refer to monocyclic or polycyclic groups having a 5- or 6-membered heteroaromatic ring containing one or more heteroatoms selected from the group consisting of O, N, and S. The 6-membered heteroaromatic ring is involved in the bonding of the adjacent group. Specific examples of heteroaromatic groups include pyridine, pyrazine, pyrimidine, pyridazine, indole, benzofuran, benzothiophene, quinoline, isoquinoline, tetrahydroquinoline, tetrahydroisoquinoline, benzothiazole, benzoxazole, benzisoxazol, thianthrene, benzimidazole, chromene, xanthene, xanthenone, xanthenol, phenoxathiin, isoindole, indolizine, cinnoline, carbazole, β-carboline, phenanthridine, acridine, phenanthroline, phenothiazine, phenoxazine, phenanthroline, isochroman, chroman, phenazine, carbazole, indoline, and isoindoline. Divalent heteroaromatic groups are obtained from the above heteroaromatic groups by removing two hydrogen atoms bonded to each heteroaromatic ring.

The following shows examples of the positions of the two bonds of the divalent heteroaromatic group of the present invention.

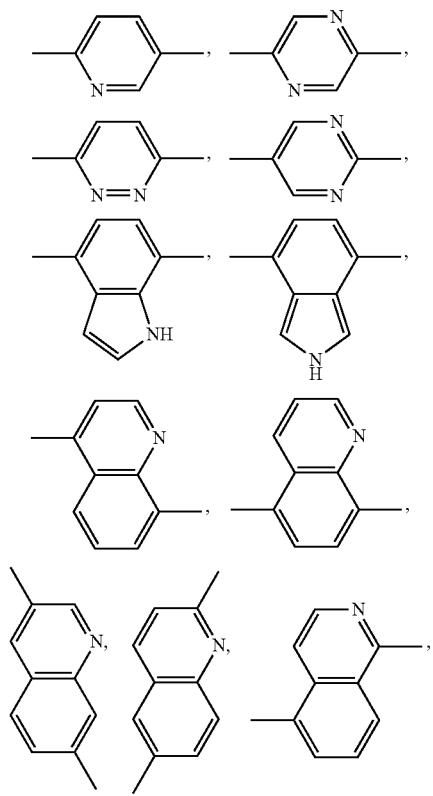

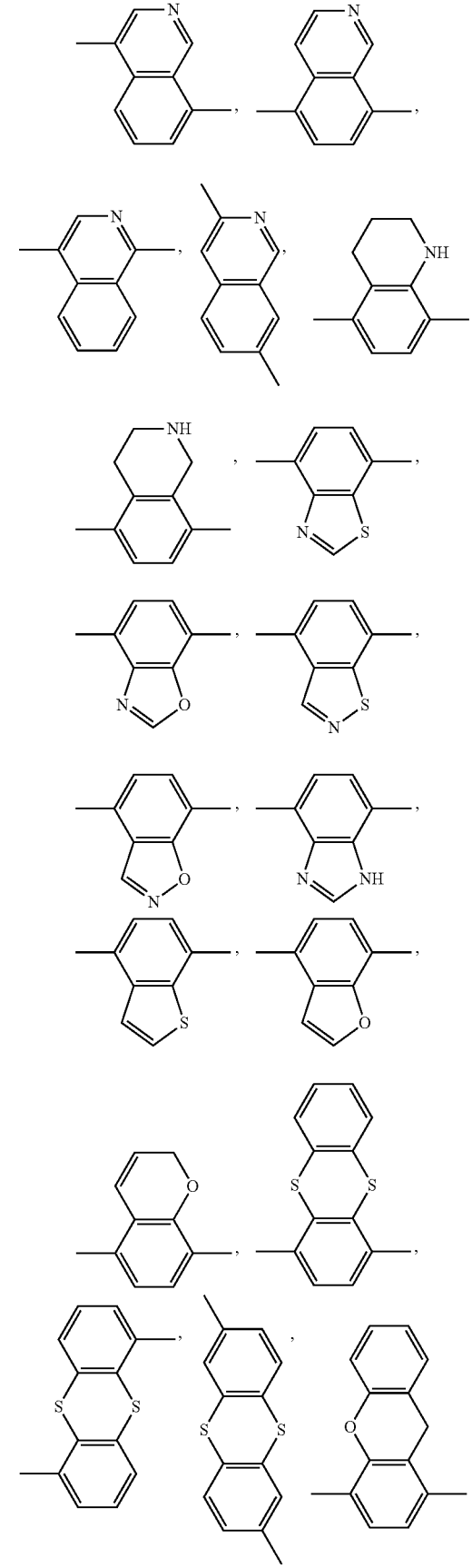

-continued
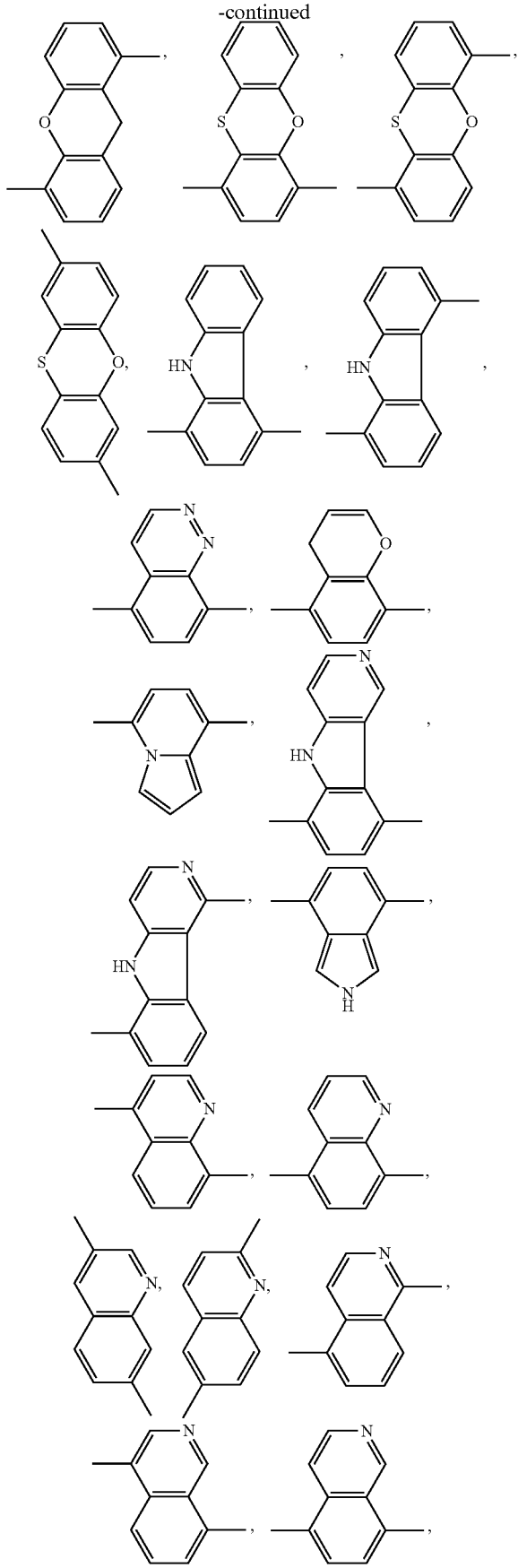
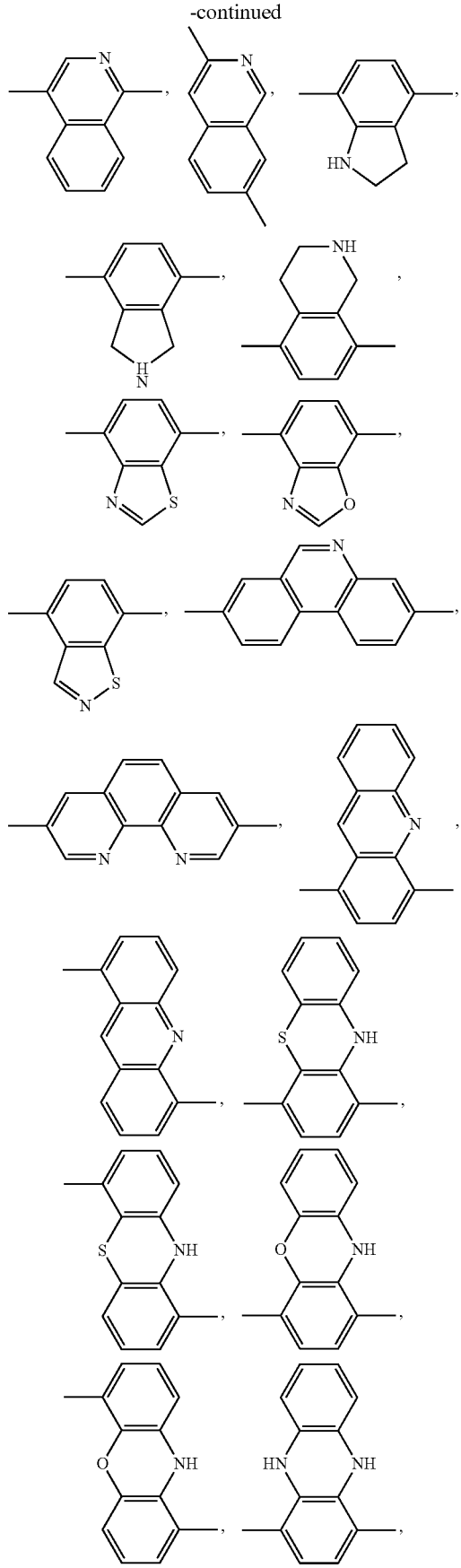

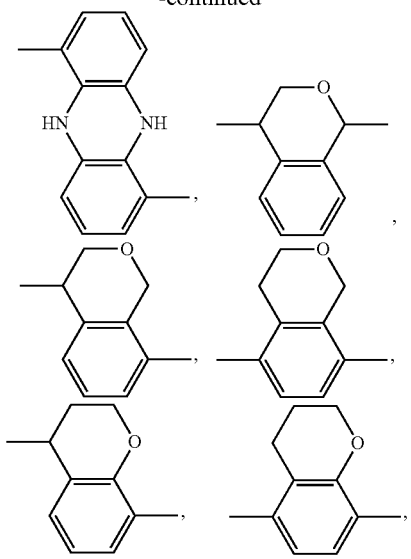

Examples of substituents for divalent aromatic groups and divalent heteroaromatic groups include the above-mentioned alkyl, cycloalkyl, alkoxy, alkenyl, alkynyl, halogen, aryl, heterocyclyl, aralkyl, OH, CN, $NO_2$, COOH, $NH_2$, monoalkylamino, dialkylamino, acylamino, acyl, alkylcarbonyloxy, arylcarbonyloxy, alkoxycarbonyl, alkoxycarbonylamino, fluoroalkyl, perfluoroalkyl, carbamoyl, mono- or di-substituted carbamoyl, sulfamoyl, mono- or di-substituted sulfamoyl, and alkylsulfonylamino. The number of substituents is 1 to 3, preferably 1 or 2, and more preferably 1.

Compounds to which electron-accepting substituents (e.g., halogen atoms, such as F, Cl, and Br; perfluoroalkyl groups, such as $CF_3$; acyl groups, such as CN, $NO_2$, COOH, and acetyl; and alkoxycarbonyl groups, such as methoxycarbonyl and ethoxycarbonyl) are bonded are suitable as electron-transfer materials. Compounds to which electron-donating substituents (e.g., alkoxy groups, such as methoxy; monoalkylamino groups, such as amino and methylamino; dialkylamino groups, such as dimethylamino; alkyl, such as OH and methyl; cycloalkyl, such as cyclopentyl; etc.) are bonded are suitable as hole-transport materials. Moreover, the compound of the present invention, which comprises a divalent aryl/heteroaryl group having an electron-accepting substituent, and a divalent aryl/heteroaryl group having an electron-donating substituent in combination is preferable as a charge-transfer material having novel properties.

n1, n2, n3, and n4 are the same or different, and represent an integer of 1 or more, preferably 1 to 30, more preferably 1 to 20, still more preferably 1 to 15, and particularly 1 to 10, 1 to 5, 1 to 4, 1 to 3, or 1 or 2.

The total of n1, n2, n3, and n4 is 4 or more, preferably about 4 to 100, 5 to 80, 6 to 60, 7 to 40, or 8 to 30, for example, 4 to 20, 4 to 19, 4 to 18, 4 to 17, 4 to 16, 4 to 15, 4 to 14, or 4 to 13. These total numbers can be obtained by suitably selecting, as starting materials, compounds having a divalent aromatic group or a divalent heteroaromatic group, and optionally isolating compounds having the target number. The purification of compounds with different totals of n1, n2, n3, and n4 can be performed by the principle of molecular sieving (e.g., gel filtration).

The compound of the present invention may be a single compound or a mixture of several compounds with different totals of n1, n2, n3, and n4.

As shows in Examples described later, when a starting material having an Ar group of the type that connects two aromatic rings, such as biphenyl or dimethylfluorene, is used, a compound having four connected Ar groups (biphenyl or dimethylfluorene) can be obtained. In contrast, when a compound having two connected aromatic rings (e.g., biphenyl) is reacted with a compound having three connected aromatic rings (e.g., triphenylene), complicated reactions occur to produce a mixture of compounds having 8 to 12, or 9 to 13 aromatic rings. To be brief, there are the following two types of reactions (Patterns A and B) that produce a —(Ar)-M(L)-(Ar)— bond.

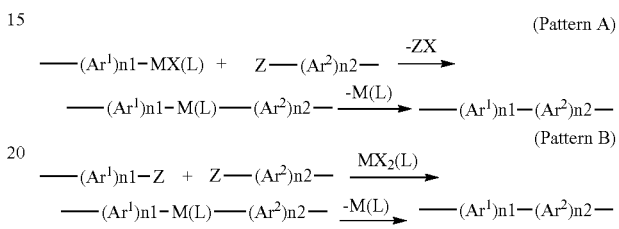

wherein $Ar^1$, $Ar^1$, M, L, n1, n2, and Z are as defined above.

As illustrated above, the reaction of MX(L) and Z, or the reaction of two Z in the presence of $MX_2(L)$ produces a $(Ar^1)n1$-M(L)-(Ar)n2 bond. Subsequently, M(L) is removed to produce a $(Ar^1)n1$-$(Ar^2)n2$ bond. Accordingly, it is considered that in the case of $(Ar^1)n1=(Ar^2)n2=(Ar^3)n3=(Ar^4)n4=$a biphenyl compound (—$C_6H_4$—$C_6H_4$—), a ring compound having 8 phenylene groups is obtained, and that in the case of $(Ar^1)n1=(Ar^3)n3=$a biphenyl compound and $(Ar^2)n2=(Ar^4)n4=$a triphenyl compound (—$C_6H_4$—$C_6H_4$—$C_6H_4$—), a ring compound having 10 (=2+3+2+3) phenylene groups (—$C_6H_4$—) is obtained. However, this reaction produces a compound having 8 to 12 or 9 to 13 phenylene groups (—$C_6H_4$—), although it depends on the reaction conditions. Thus, polygon structures may be involved.

The key to the synthesis of the compound of the present invention is to fold a para(hetero)arylene compound, which has the most stable planar structure, to form a circular shape. This time, a stable metal complex (particularly a platinum complex) having a square structure, as shown by Formula (III) or (IV), or a polygon structure was used as a precursor of cycloparaphenylene, thereby establishing an efficient synthesis method of cyclopara(hetero)arylene. The square structure represented by Formula (III) or (IV) is considered to be an intermediate in the production of [8]cycloparaphenylene with 4×4; however, polygon structures may be involved in the production of [9]-[13] cycloparaphenylenes. The present inventor does not wish to be restricted by theory, but assumes that quadrate complexes are produced from one type of compound, and that polygon complexes, including square complexes, are produced when substituents having different shapes (lengths) are mixed.

The synthesis of stable metal complexes with a square structure includes three roots. The first route is to synthesize a complex in one step from four metallized aromatic compounds (Z—$(Ar^1)_{n1}$—Z, Z—$(Ar^2)_{n2}$—Z, Z—$(Ar^3)_{n3}$—Z, and Z—$(Ar^4)_{n4}$—Z). The compound of Formula (I) of the present invention is obtained from this route (Scheme 1, route a). The second route is to synthesize a complex in one step from one metallized aromatic compound (Z—$(Ar^1)_{n1}$—Z). This route is suitable for the synthesis of [4×n1]cyclopara (hetero)arylene (Scheme 1, route b). The other route is to synthesize a metal complex (preferably a platinum complex)

in two steps. This route is suitable for the synthesis of various cycloparaphenylenes with an odd number of rings (Scheme 1, route c). Cyclopara(hetero)arylene can be obtained with a high yield by reductive elimination of the metal complex (particularly platinum complex).

Further, Scheme 2 shows other examples of routes b and c of Scheme 1 using a heteroparaphenylene derivative as a starting material.

In route a of Scheme 1, $Z$—$(Ar^1)_{n1}$—$Z$, $Z$—$(Ar^2)_{n2}$—$Z$, $Z$—$(Ar^3)_{n3}$—$Z$, and $Z$—$(Ar^4)_{n4}$—$Z$ are reacted with $MX_2(L)$ to obtain a compound (III), and M(L), particularly Pt(L), is eliminated from the compound (III) directly or in the presence of a neutral ligand, such as triphenylphosphine, or halogen, such as $Br_2$ (or may be $I_2$), thereby obtaining a target compound (I). The reaction for obtaining the compound (III) by reacting $Z$—$(Ar^1)_{n1}$—$Z$, $Z$—$(Ar^2)_{n2}$—$Z$, $Z$—$(Ar^3)_{n3}$—$Z$, and $Z$—$(Ar^4)_{n4}$—$Z$ with $MX_2(L)$ can advantageously proceed by performing the reaction at a temperature of −78° C. to the boiling point of the solvent for about 30 minutes to 24 hours. When a solvent is used, usable examples include ether-based solvents, such as diethyl ether and tetrahydrofuran; halogen-based solvents, such as methylene chloride and 1,2-dichloroethane; and hydrocarbon-based solvents, such as benzene and toluene. The amount of $MX_2(L)$ used is about 1 mole per mole of the total amount of $Z$—$(Ar^1)_{n1}$—$Z$, $Z$—$(Ar^2)_{n2}$—$Z$, $Z$—$(Ar^3)_{n3}$—$Z$, and $Z$—$(Ar^4)_{n4}$—$Z$.

Subsequently, the compound (III) is reacted in the presence or absence of a solvent (e.g., an ether-based solvent, such as tetrahydrofuran or dioxane; a hydrocarbon-based solvent, such as toluene or mesitylene; or a halogen-based solvent, such as 1,2-dichloroethane or 1,2-dichlorobenzene) at room temperature to about 200° C. for about 1 to 48 hours to eliminate M(L), particularly Pt(L), thereby obtaining a target cyclopara(hetero)arylene compound (I). In this reaction, halogen, such as $Br_2$ (or $I_2$), or a neutral ligand, such as triphenylphosphine, can be used in an amount of 4 moles to excess moles per mole of the compound (III).

In route b of Scheme 1, $Z$—$(Ar^1)_{n1}$—$Z$ is reacted with $MX_2(L)$ to obtain a compound (IIIa), and ML, particularly Pt(L), is eliminated from the compound (III) in the presence of halogen, such as $Br_2$ (or $I_2$), thereby obtaining a target cyclopara(hetero)arylene compound (Ia). $MX_2(L)$ is used in an amount of about 1 mole per mole of $Z$—$(Ar^1)_{n1}$—$Z$, and the reaction is carried out at a temperature of −78° C. to the boiling temperature of the solvent for about 30 minutes to 24 hours, thereby obtaining a compound (IIIa). When a solvent is used, usable examples include ether-based solvents, such as diethyl ether and tetrahydrofuran. Subsequently, halogen, such as $Br_2$ (or $I_2$), is used in an amount of 1 mole to excess moles per mole of the compound (IIIa), and they are reacted optionally in the presence of a solvent (e.g., an ether-based solvent, such as diethyl ether or tetrahydrofuran) at room temperature to about 100° C. for about 1 to 24 hours to eliminate M(L), particularly Pt (L), thereby obtaining a target cyclopara(hetero)arylene (Ia).

In route c of Scheme 1, 2 moles or more of $MX_2(L)$ is reacted with 1 mole of $Z$—$(Ar^1)_{n1}$—$Z$ at a temperature of −78° C. to the boiling point of the solvent for about 30 minutes to 24 hours, thereby obtaining a compound in which Z is substituted with MX(L). The resulting compound is then reacted with an almost equimolar amount of $Z$—$(Ar^2)_{n2}$—$Z$ at a temperature of −78° C. to the boiling point of the solvent for about 30 minutes to 24 hours, thereby obtaining a compound (IIIb). When a solvent is used, usable examples include ether-based solvents, such as diethyl ether and tetrahydrofuran. Subsequently, halogen, such as $Br_2$ (or $I_2$) is used in an amount of 1 mole to excess moles per mole of the compound (IIIb), and they are reacted optionally in the presence of a solvent (e.g., an ether-based solvent, such as diethyl ether or tetrahydrofuran) at room temperature to about 100° C. for about 1 to 24 hours to eliminate ML, particularly Pt(L), thereby obtaining a target cyclopara(hetero)arylene (Ib).

Routes b and c of Scheme 2 can advantageously proceed by performing the reactions under the same conditions as those of routes b and c of Scheme 1.

<Scheme 1> a)

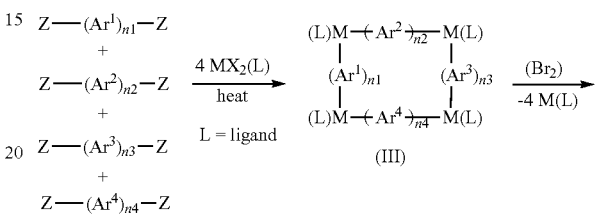

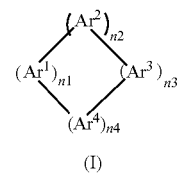

b)

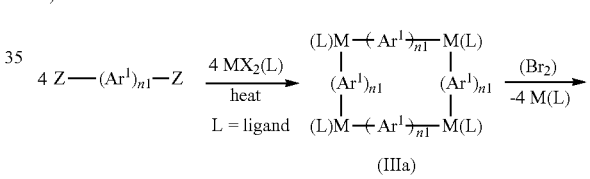

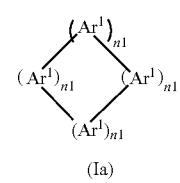

c)

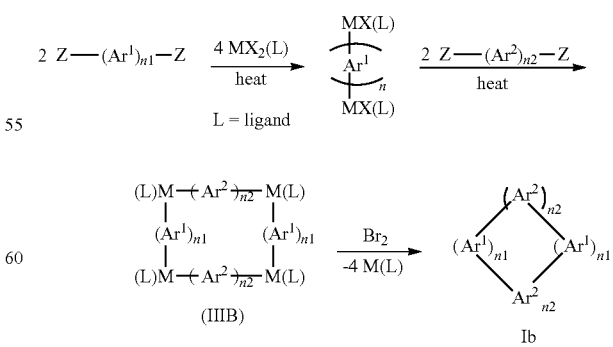

wherein $Ar^1$, $Ar^2$, $Ar^3$, $Ar^4$, n1, n2, n3, n4, M, L, X, and Z are as defined above.

<Scheme 2> b)

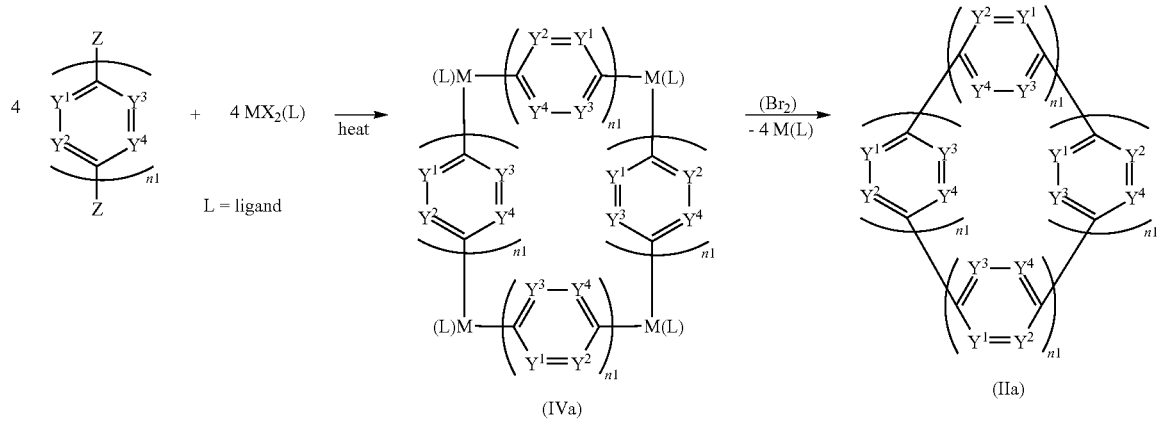

(IVa) → (IIa)

c)

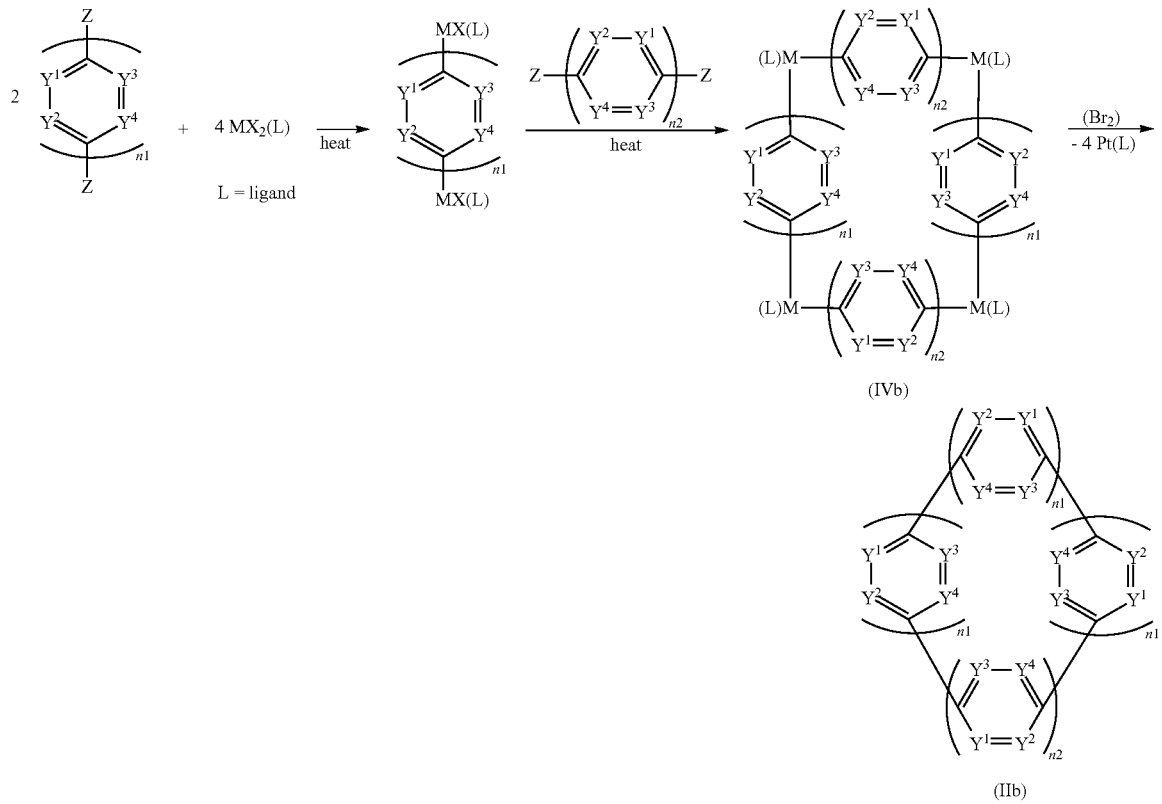

(IVb)

(IIb)

wherein $Y^1$, $Y^2$, $Y^3$, $Y^4$, n1, n2, M, X, L, and Z are as defined above.

Schemes 1 and 2 above show examples where rearrangement reactions or reactions of pentagonal or more polygonal structures do not occur. In the case of n1=n2=n3=n4=2, the compound of the present invention, to which 8 aryl/heteroaryl groups (Ar) are bonded, is theoretically obtained; however, when n2, n3, or n4 include three or more aryl/heteroaryl groups, complicated rearrangement reactions or reactions that produce polygon structures occur, and mixtures of compounds having various numbers of aryl groups are obtained. The target compound can be obtained by purifying these mixtures.

Accordingly, the compounds exemplified in this specification represented by the formulae including four (hetero)aryl units (($Ar^1$)n1, ($Ar^2$)n2, ($Ar^3$)n3, and ($Ar^4$)n4), and optionally including four or more metals M(L), can be compounds including five or more (hetero)aryl units (($Ar^1$)n1, ($Ar^2$)n2, ($Ar^3$)n3, ($Ar^4$)n4, ($Ar^5$)n5...), and optionally including five or more metals M(L).

In the case of the compounds of Formulae (I) and (II), even when they are ring compounds having five or more (hetero)aryl units, the present invention includes compounds contained in these formulae. In the case of the compounds of Formulae (III) and (IV), the present invention includes compounds having the same number and five or more (hetero)aryl units and metals M(L).

EXAMPLES

The present invention is described in detail below using Examples. Needless to say, however, the present invention is not limited to these Examples.

Example 1

Selective synthesis of [8]cycloparaphenylene (3)

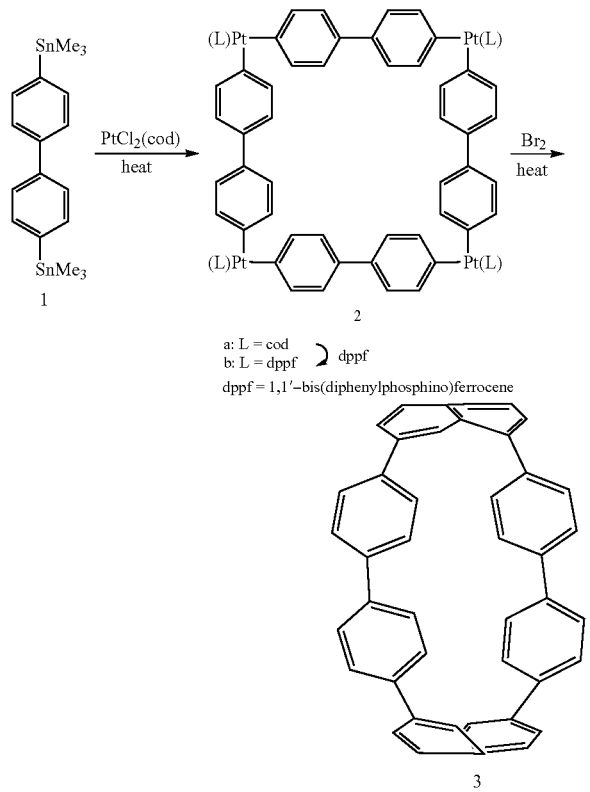

Synthesis of [(cod)Pt(4,4'-biphenyl)]$_4$ (2a) (cod=1,5-cyclooctadiene)

4,4'-bis(trimethylstannyl)biphenyl (1)[1] (298 mg, 0.621 mmol) and Pt(cod)Cl$_2$ (233 mg, 0.623 mmol) were dissolved in 150 mL of 1,2-dichloroethane under nitrogen airflow, and the resulting solution was stirred under heating at 70° C. for 59 hours. The produced precipitate was separated by filtration. The collected solid was washed with hexane and then washed with a small amount of methylene chloride, thereby obtaining a compound 2a as a light-yellow solid with a yield of 51% (145.2 mg, 0.317 mmol).

$^1$H NMR (400 MHz, CD$_2$Cl$_2$) δ2.52 (bs, 32 H), 5.10 (bs, 16 H), 7.12 (d, J=6.8 Hz, 16 H), 7.19 (d, J=8.0 Hz, 16 H); $^{13}$C NMR (100 MHz, CD$_2$Cl$_2$) 30.1, 104.8, 125.6, 135.0, 136.1, 154.3; MS (FAB) m/z calcd for C$_{80}$H$_{80}$Pt$_4$(M)$^+$ 1820.5, found 1820.4.

Synthesis of [(dppf)Pt(4,4'-biphenyl)]$_4$ (2b)

The compound 2a (31.1 mg, 17.0 μmol) and 1,1-bis(diphenylphosphino)ferrocene (dppf, 39.5 mg, 71.2 μmol) were suspended in 10 mL of methylene chloride under nitrogen airflow, and stirred at room temperature for 6 hours. After the solvent was removed under reduced pressure, the residue was washed with ethyl acetate, thereby obtaining a compound 2b as a light-orange solid with a yield of 91% (55.8 mg, 15.5 μmol).

$^1$H NMR (400 MHz, CD$_2$Cl$_2$) 4.20 (bs, 16 H), 4.29 (bs, 16 H), 6.37 (d, J=7.6 Hz, 16 H), 6.69 (m, 16 H), 7.21 (t, 32 H), 7.31 (t, 16H), 7.48 (t, 32 H).

When the compound 2a was not isolated, and the obtained solid was used in the subsequent step as it was, a compound 2b was obtained with a yield of 74% (total of two steps).

Synthesis of [8]cycloparaphenylene (3)

The compound 2b (24.2 mg, 6.71 μmol) was suspended in 5 mL of toluene under nitrogen airflow, and bromine (3 μL, 49 μmol) was added thereto at room temperature. After the reaction solution was stirred at 95° C. for 17 hours, insoluble substances were filtered off. The solvent of the filtrate was removed under reduced pressure to thereby obtain a solid. The resulting solid was purified by preparative gel filtration chromatography (GPC; mobile phase: chloroform), and then further purified by silica gel column chromatography (mobile phase: a mixed solution of chloroform/hexane at a ratio of 1/4 to 1/1), thereby obtaining a compound 3 as a yellow solid with a yield of 49% (2.0 mg, 3.29 μmol.)

$^1$H NMR (400 MHz, CDCl$_3$) δ7.48 (s, 32 H); $^{13}$C NMR (100 MHz) 127.6, 137.8; MS (MALDI-TOF) m/z calcd for C$_{48}$H$_{32}$ (M)$^+$ 608.2505, found 608.2504.

The following table shows comparisons of the above experiment with experiments using PPh$_3$ or I$_2$ in place of bromine. The reaction conditions (solvent and temperature) were the same as those for bromine.

TABLE 1

| Entry | Reagent (equiv) | Reaction time (h) | Yield (%) | (Note) |
|---|---|---|---|---|
| 1 | Br$_2$ (7) | 17 | 49 | Above results |
| 2 | I$_2$ (7) | 24 | 5.3 | |
| 3 | PPh$_3$ (9) | 24 | 2.6 | |

Alternative method of selective synthesis of [8]cycloparaphenylene (3) (actually, alternative method of the synthesis of the compound 2)

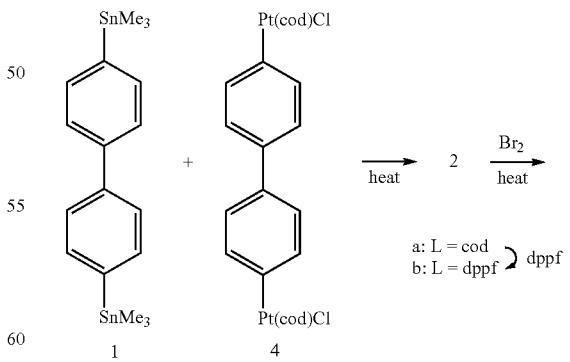

The compound 1 (246 mg, 0.511 mmol) and a platinum complex 4 (di-μ-[1,1'-biphenyl]-4,4'-diyldichlorobis[(1,2,5,6-η)-1,5-cyclooctadiene]diplatinum)[2] (416 mg, 0.501 mmol) were dissolved in 250 mL of 1,2-dichloroethane under nitrogen airflow, and the resulting solution was stirred at 50°

C. for 7 days. After insoluble substances were filtered off, the solvent of the filtrate was removed under reduced pressure to thereby obtain a solid. The solid was washed with hexane, thereby obtaining a compound 2a as a light-yellow solid (421 mg). This compound was used as it was, without purification, in the subsequent step.

A mixture of the compound 2a (70 mg) and dppf (89 mg, 0.16 mmol) was suspended in 20 mL of methylene chloride under nitrogen airflow, and stirred at room temperature for 17 hours. After the solvent was removed, the obtained solid was washed with ethyl acetate, thereby obtaining a compound 3 as a light-orange solid (103.6 mg).

Example 2

Synthesis of [9], [10], [11], [12], and [13] cycloparaphenylenes

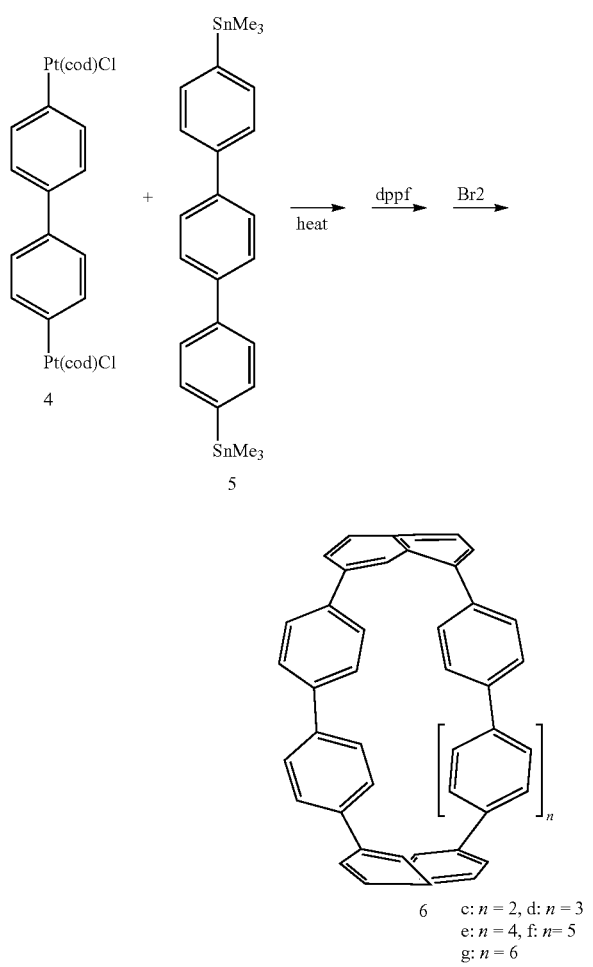

6  c: $n = 2$, d: $n = 3$
   e: $n = 4$, f: $n = 5$
   g: $n = 6$

The compound 4 (58.2 mg, 70.2 μmol) and the compound 5 (1,1'-[1,1':4',1''-terphenyl]-4,4''-diyl[1,1,1-trimethyl-stanane]) (40.8 mg, 73.4 μmol) were dissolved in 30 mL of 1,2-dichloroethane under nitrogen airflow, and heated at 50° C. for 20 hours. After the solid was filtered off, the solvent of the filtrate was removed under reduced pressure. The obtained solid was washed with hexane, thereby obtaining 59.8 mg of platinum complex with a ring structure as a light-yellow solid.

The obtained solid (31.1 mg, 17.0 μmol) and dppf (53.3 mg, 97.9 μmol) were suspended in 10 mL of methylene chloride under nitrogen airflow, and stirred at room temperature for 17 hours. After the solvent was removed under reduced pressure, the residue was washed with ethyl acetate, thereby obtaining 79.3 mg of dppf-coordinated ring platinum complex as a light-orange solid.

The obtained solid (52.0 mg) was suspended in 5 mL of toluene under nitrogen airflow, and bromine (5 μL, 98 μmol) was added thereto at room temperature. After the reaction solution was stirred at 90° C. for 1 hour, insoluble substances were filtered off. The solvent of the filtrate was removed under reduced pressure to thereby obtain a solid. The obtained solid was purified by silica gel column chromatography (mobile phase: a mixed solution of chloroform/hexane at a ratio of 1/4 to 1/1). Analysis of the resulting product by $^1$H NMR showed that [9]-, [10]-, [11]-, [12]-, and [13]-cycloparaphenylenes (6a to 6e) were produced with yields of 5.4%, 9.6%, 7.7%, 3.8%, and 0.8%, respectively (total yield of three steps based on the compound 4).

[9]-Cycloparaphenylene (6a): $^1$H NMR (400 MHz, CDCl$_3$) 7.52 (s, 36H); MS (MALDI-TOF) m/z calcd for $C_{54}H_{36}$ (M)$^+$ 684.3, found 684.3.

[10]-Cycloparaphenylene (6b): $^1$H NMR (400 MHz, CDCl$_3$) 7.56 (s, 40H); MS (MALDI-TOF) m/z calcd for $C_{60}H_{40}$ (M)$^+$ 760.3, found 760.3.

[11]-Cycloparaphenylene (6c): $^1$H NMR (400 MHz, CDCl$_3$) 7.58 (s, 44H); MS (MALDI-TOF) m/z calcd for $C_{66}H_{44}$ (M)$^+$ 836.3, found 836.4.

[12]-Cycloparaphenylene (6d): $^1$H NMR (400 MHz, CDCl$_3$) 7.61 (s, 48H); MS (MALDI-TOF) m/z calcd for $C_{72}H_{48}$ (M)$^+$ 912.4, found 912.5.

[13]-Cycloparaphenylene (6e): $^1$H NMR (400 MHz, CDCl$_3$) 7.64 (s, 52H).

Large-Scale Synthesis

The compound 4 (501 mg, 0.604 mmol) and the compound 5 (335 mg, 0.603 mmol) were dissolved in 300 mL of 1,2-dichloroethane under nitrogen airflow, and heated at 50° C. for 32 hours. After the solid was filtered off, the solvent of the filtrate was removed under reduced pressure. The obtained solid was washed with hexane, thereby obtaining 641 mg of platinum complex with a ring structure as a light-yellow solid. The solid and dppf (630 mg, 1.23 mmol) were suspended in 100 mL of methylene chloride under nitrogen airflow, and stirred at room temperature for 14 hours. After the solvent was removed under reduced pressure, the residue was washed with ethyl acetate, thereby obtaining a dppf-coordinated ring platinum complex as a light-orange solid. The solid was suspended in 85 mL of toluene, and bromine (62 μL, 1.21 mmol) was added thereto at room temperature. After the reaction solution was stirred at 90° C. for 12 hours, insoluble substances were filtered off. The solvent of the filtrate was removed under reduced pressure to thereby obtain a solid. The obtained solid was purified by silica gel column chromatography (mobile phase: a mixed solution of chloroform/hexane at a ratio of 1/4 to 1/1). The $^1$H NMR analysis showed that [8]-, [9]-, [10]-, [11]-, and [12]-cycloparaphenylenes were produced with yields of 2.4%, 3.2%, 5.3%, 4.7%, and 2.3%, respectively. Further, each cycloparaphenylene was isolated by purification by preparative gel filtration chromatography (GPC; mobile phase: chloroform).

Example 3

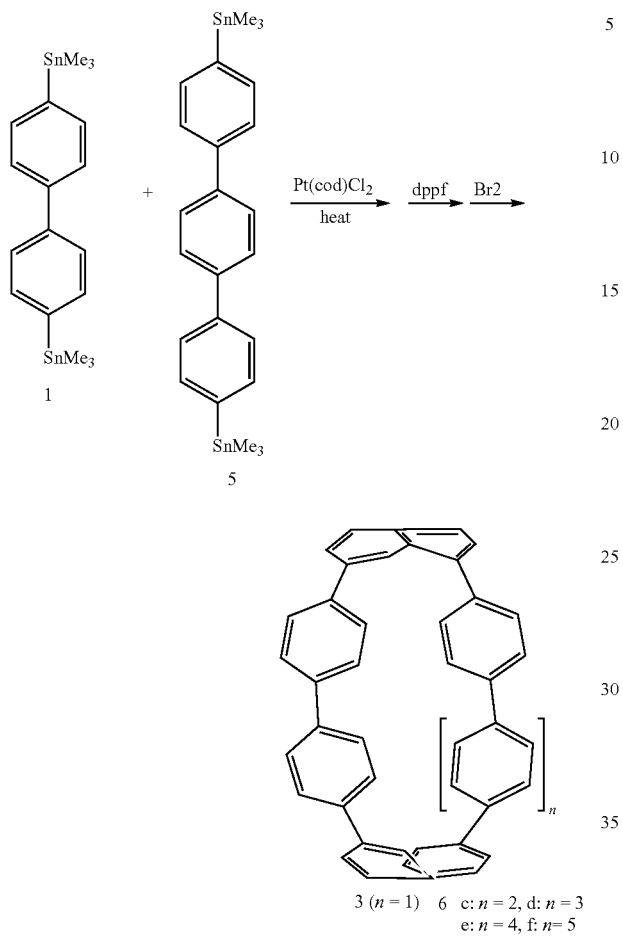

3 (n = 1) 6 c: n = 2, d: n = 3
e: n = 4, f: n = 5

The compound 1 (32.1 mg, 0.0668 mmol), the compound 5 (37.1 mg, 0.0668 mmol), and Pt(cod)Cl$_2$ (50 mg, 0.1336 mmol) were dissolved in 35 mL of 1,2-dichloroethane under nitrogen airflow, and stirred at 70° C. for 24 hours. After the solvent was removed, the generated solid was washed with hexane. Methylene chloride was added to the solid, and the solid was filtered. The methylene chloride solution was removed under reduced pressure, thereby obtaining a white solid (71.2 mg).

The obtained solid (30 mg) was taken, and dppf (31.8 mg, 0.05743 mmol) was added thereto. The resulting mixture was then suspended in 10 mL of methylene chloride under nitrogen airflow, and stirred at room temperature for 24 hours. After the solvent was removed, the residue was washed with ethyl acetate to thereby obtain a solid (56.0 mg).

The obtained solid (23.8 mg) was taken, and 3.75 mL of toluene was added thereto. To the resultant mixture was added 1.25 mL of Br$_2$ toluene solution ($1.95 \times 10^{-2}$ mol/L), and then the mixture was stirred at 95° C. for 12 hours. After the reaction solution was passed through an alumina column (mobile phase: a mixed solution of chloroform/hexane at a ratio of 1/4 to 1/1), the solvent was removed. The $^1$H NMR analysis of the reaction product showed that [8]-, [9]-, [10]-, [11]-, and [12]-cycloparaphenylenes were produced with yields of 0.7%, 3.0%, 7.3%, 9.8%, and 3.7%, respectively.

Example 4

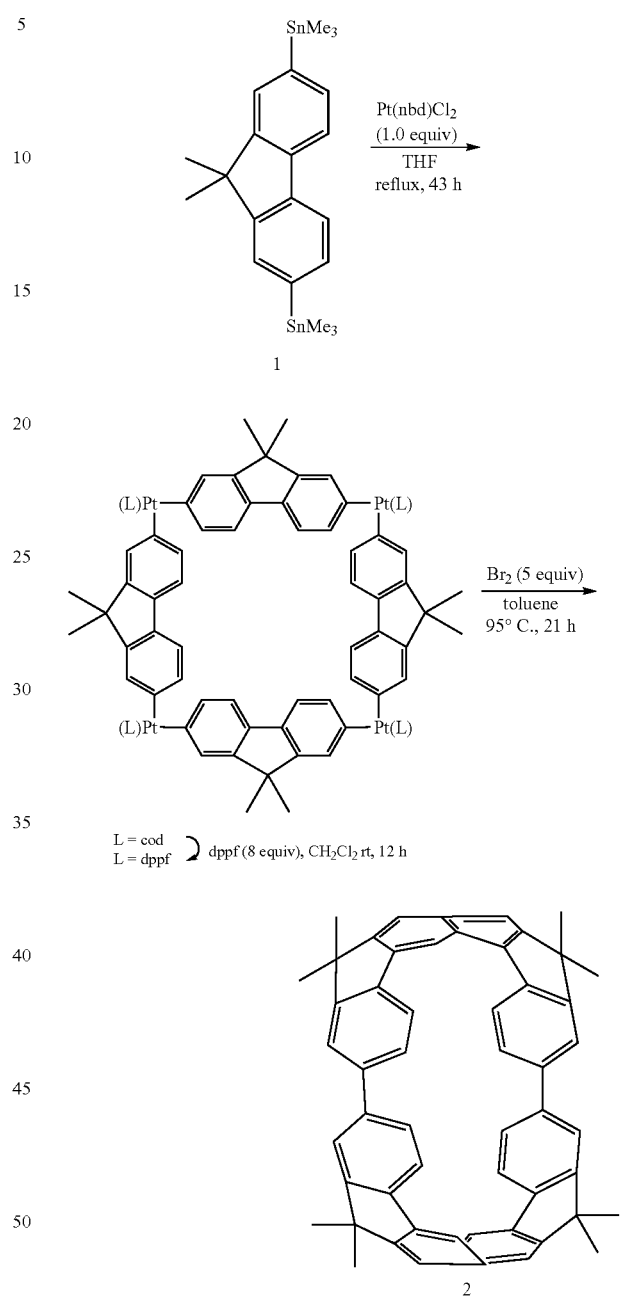

The compound 1 (9,9-dimethyl-9H-fluorene-2,7-diyl)bis (trimethylstannane) (104 mg, 0.2 mmol) and [(nbd)Pt(4,4'-biphenyl)]$_4$ (72 mg, 0.2 mmol) were dissolved in 150 mL of THF under nitrogen airflow, and heated at 66° C. for 43 hours. After the solvent was evaporated under reduced pressure, the solid was washed with ethyl acetate, thereby obtaining a light-orange solid (100 mg). The solid and dppf (231 mg, 0.42 mmol) were suspended in 67 mL of methylene chloride under nitrogen airflow, and stirred at room temperature for 12 hours. After the solvent was removed under reduced pressure, the solid was washed with ethyl acetate, thereby obtaining a light-orange solid (44.2 mg). After the solid was suspended in 25 mL of toluene under nitrogen airflow, bromine (6.8 μL, 0.13 mmol) was added at room temperature. After the reaction solution was heated at 95° C. for 21 hours, the solvent was removed under reduced pressure. The crude product was purified by silica gel chromatography (mobile phase: a solution of methylene chloride/hexane at a ratio of 1/1), and further purified by preparative gel filtration chromatography (GPC; mobile phase: chloroform). Thus, a compound 2 was obtained with a yield of 11% (0.85 mg).

$^1$H NMR (400 MHz, CDCl$_3$) 1.17 (s, 12H), 6.89 (s, 8 H), 7.52 (d, 8 H), 7.58 (d, 8 H); $^{13}$C NMR (100 MHz, CDCl$_3$) 23.9, 31.7 122.2, 123.9, 126.6, 138.3, 139.7 157.2; MS (MALDI-TOF) m/z calcd for C$_{60}$H$_{48}$(M)$^+$ 768.376, found 768.366.

References

[1] M. D. Curtis, A. L. Allred, J. Am. Chem. Soc. 1965, 87, 2554.

[2] D. C. Caskey, R. K. Shoemaker, J. Michl, Org. Lett. 2004, 6, 2093.

Industrial Applicability

The compound of the present invention, which has fluorescence, provides a novel skeleton for the development of organic electronic devices, such as organic EL, organic transistors, and organic solar cell materials. Additionally, the compound of the present invention is expected to be applied to various nanotechnology materials, such as photonic and electronic materials, for which the use of carbon nanotubes is being considered.

The invention claimed is:

1. A compound represented by Formula (I):

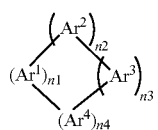
(I)

wherein Ar$^1$, Ar$^2$, Ar$^3$, and Ar$^4$ are the same or different, and represent an optionally substituted divalent aromatic group, and n1, n2, n3, and n4 are the same or different, and represent an integer of 1 to 30, with the proviso that in the case of Ar$^1$=Ar$^2$=Ar$^3$=Ar$^4$=1,4-phenylene, n1+n2+n3+n4 is a number other than 9, 12, and 18.

2. The compound according to claim 1 represented by Formula (II):

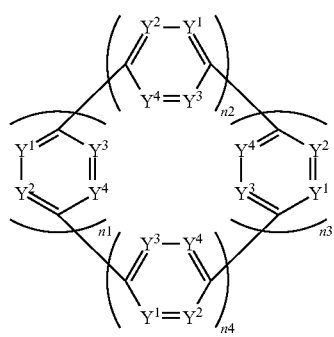
(II)

wherein Y$^1$ is the same or different, and represents CR$^1$,
Y$^2$ is the same or different, and represents CR$^2$,
Y$^3$ is the same or different, and represents CR$^3$,
Y$^4$ is the same or different, and represents CR$^4$, R$^1$, R$^2$, R$^3$, and R$^4$ are the same or different, and represent hydrogen, alkyl, cycloalkyl, alkoxy, alkenyl, alkynyl, halogen, aryl, heterocyclyl, aralkyl, OH, CN, NO$_2$, COOH, NH$_2$, monoalkylamino, dialkylamino, acylamino, acyl, alkylcarbonyloxy, arylcarbonyloxy, alkoxycarbonyl, alkoxycarbonylamino, fluoroalkyl, perfluoroalkyl, carbamoyl, mono- or di-substituted carbamoyl, sulfamoyl, mono- or di-substituted sulfamoyl, or alkylsulfonylamino; adjacent R$^1$ and R$^2$, or R$^3$ and R$^4$, together with the carbon atoms to which they are attached, may form an optionally substituted 5- or 6-membered ring group, and n1, n2, n3, and n4 are the same or different, and represent an integer of 1 to 30, with the proviso that in the case of Y$^1$=Y$^2$=Y$^3$=Y$^4$=CH, n1+n2+n3+n4 is a number other than 9, 12, and 18.

3. The compound according to claim 1, wherein the divalent aromatic group is derived from an aromatic group selected from the group consisting of benzene, naphthalene, fluorene, indane, indene, azulene, anthracene, phenanthrene, phenalene, dihydroanthracene, indacene, dibenzosuberane, tetracene, and pyrene.

4. A compound represented by the following Formula (III):

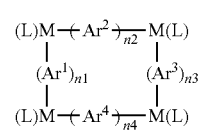
(III)

wherein Ar$^1$, Ar$^2$, Ar$^3$, and Ar$^4$ are the same or different, and represent an optionally substituted divalent aromatic group, M is the same or different, and represents Pt, Pd, or Ni, L is the same or different, and represents a ligand capable of coordinating with M, provided that, when M is Pt, L represents cyclooctadiene (cod), norbornadiene (nbd), ethylenediamine, and N-alkyl derivatives thereof, 2,2'-, 3,3'-, 4,4'-, 2,3'-, 2,4'-, or 3,4'-bipyridine, or alkyl-substituted derivatives thereof; 1,10-phenanthroline, triphenylphosphine, tributylphosphine, dimethylphenylphosphine, 1,1'-bis(diaryl)ferrocenylphosphine, such as 1,1'-bis(diphenylphosphino)ferrocene (dppf); diarylphosphinoethane, such as diphenylphosphinoethane; diphenylphosphinobutane, Xantphos, 2,2'-bis(diphenylphosphino)-1,1'-binaphthalene, tricyclohexylphosphine, cyclododecatriene, norbornene, 1,5-hexadiene, benzonitrile, butadiene, dimethyl acetylenedicarboxylate, dibenzylideneacetone, 1,5-bis(diphenylphosphino)pentane, diphenylmethylphosphine, and derivatives thereof, and n1, n2, n3, and n4 are the same or different, and represent an integer of 1 to 30.

5. The compound according to claim 4 represented by the following Formula (IV):

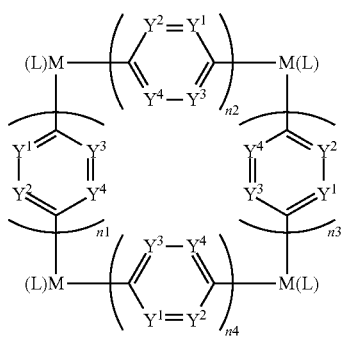

(IV)

wherein M is the same or different, and represents Pt, Pd, or Ni,

L is the same or different, and represents a ligand capable of coordinating with M, $Y^1$ is the same or different, and represents $CR^1$,
$Y^2$ is the same or different, and represents $CR^2$,
$Y^3$ is the same or different, and represents $CR^3$,
$Y^4$ is the same or different, and represents $CR^4$, $R^1$, $R^2$, $R^3$, and $R^4$ are the same or different, and represent hydrogen, alkyl, cycloalkyl, alkoxy, alkenyl, alkynyl, halogen, aryl, heterocyclyl, aralkyl, OH, CN, $NO_2$, COOH, $NH_2$, monoalkylamino, dialkylamino, acylamino, acyl, alkylcarbonyloxy, arylcarbonyloxy, alkoxycarbonyl, alkoxycarbonylamino, fluoroalkyl, perfluoroalkyl, carbamoyl, mono- or, di-substituted carbamoyl, sulfamoyl, mono- or di-substituted sulfamoyl, or alkylsulfonylamino; adjacent $R^1$ and $R^2$, or $R^3$ and $R^4$, together with the carbon atoms to which they are attached, may form an optionally substituted 5- or 6-membered ring group, and n1, n2, n3, and n4 are the same or different, and represent an integer of 1 to 30.

6. A method for producing a compound of Formula (I), comprising eliminating M(L) from a compound of Formula (III):

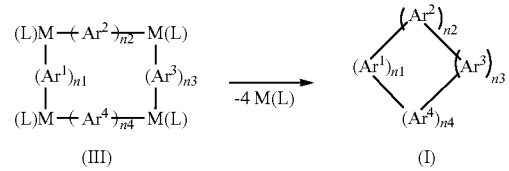

wherein $Ar^1$, $Ar^2$, $Ar^3$, and $Ar^4$ are the same or different, and represent an optionally substituted divalent aromatic group, n1, n2, n3, and n4 are the same or different, and represent an integer of 1 to 30, M is the same or different, and represents Pt, Pd, or Ni, and L is the same or different, and represents a ligand capable of coordinating with M.

\* \* \* \* \*